(12) United States Patent
Rampersaud et al.

(10) Patent No.: US 9,480,520 B2
(45) Date of Patent: Nov. 1, 2016

(54) SURGICAL INSTRUMENT AND METHOD

(71) Applicant: Warsaw Orthopedic, Inc., Warsaw, IN (US)

(72) Inventors: Y. Raja Rampersaud, Toronto (CA); William Allan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 85 days.

(21) Appl. No.: 14/162,319

(22) Filed: Jan. 23, 2014

(65) Prior Publication Data
US 2015/0201985 A1   Jul. 23, 2015

(51) Int. Cl.
*A61B 17/58* (2006.01)
*A61B 17/88* (2006.01)
*A61B 17/70* (2006.01)

(52) U.S. Cl.
CPC ....... *A61B 17/8875* (2013.01); *A61B 17/7032* (2013.01); *A61B 17/7074* (2013.01); *A61B 17/7082* (2013.01); *A61B 17/8897* (2013.01)

(58) Field of Classification Search
CPC .......... A61B 17/7074; A61B 17/7079; A61B 17/708; A61B 17/7085; A61B 17/8875
USPC ....... 606/86 A, 104, 96, 916, 279, 304, 305, 606/318, 329
See application file for complete search history.

(56) References Cited

U.S. PATENT DOCUMENTS

| | | | | | |
|---|---|---|---|---|---|
| 2,121,193 | A | * | 6/1938 | Hanicke | A61B 17/742 408/215 |
| 4,341,206 | A | * | 7/1982 | Perrett | A61B 17/1721 606/102 |
| 6,827,722 | B1 | * | 12/2004 | Schoenefeld | A61B 17/1622 606/104 |
| 6,955,678 | B2 | * | 10/2005 | Gabriel | A61B 17/1714 606/104 |
| 7,137,985 | B2 | * | 11/2006 | Jahng | A61B 17/3421 606/279 |
| 7,604,643 | B2 | * | 10/2009 | Ciccone | A61B 17/1615 606/104 |
| 8,075,579 | B2 | * | 12/2011 | Hamada | A61B 17/1671 606/167 |
| 2013/0310842 | A1 | * | 11/2013 | Winkler | A61B 17/8897 606/104 |
| 2014/0276892 | A1 | * | 9/2014 | Pakzaban | A61B 17/8875 606/104 |

* cited by examiner

*Primary Examiner* — Pedro Philogene
*Assistant Examiner* — David C Comstock

(57) ABSTRACT

A surgical instrument includes a lock including an inner surface defining a cavity and a locking surface. A holding element is positioned within the cavity and includes an inner surface defining a passageway. A longitudinal element is positioned within the passageway and the cavity. The surgical instrument includes a first orientation in which a distal end of the holding element is spaced apart from the locking surface and the longitudinal element is translatable relative to the holding element and a second orientation in which the distal end of the holding element engages the locking surface and the longitudinal element is fixed relative to the holding element. Systems and methods are disclosed.

20 Claims, 12 Drawing Sheets

SURGICAL INSTRUMENT AND METHOD

TECHNICAL FIELD

The present disclosure generally relates to medical devices for the treatment of musculoskeletal disorders, and more particularly to a surgical system for delivering and/or fastening implants with a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attaching rods and plates to the exterior of two or more vertebral members. This disclosure describes an improvement over these prior art technologies.

SUMMARY

In one embodiment, a surgical instrument is provided. The surgical instrument includes a lock including an inner surface defining a cavity and a locking surface. A holding element is positioned within the cavity and includes an inner surface defining a passageway. A longitudinal element is positioned within the passageway and the cavity. The surgical instrument includes a first orientation in which a distal end of the holding element is spaced apart from the locking surface and the longitudinal element is translatable relative to the holding element and a second orientation in which the distal end of the holding element engages the locking surface and the longitudinal element is fixed relative to the holding element. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
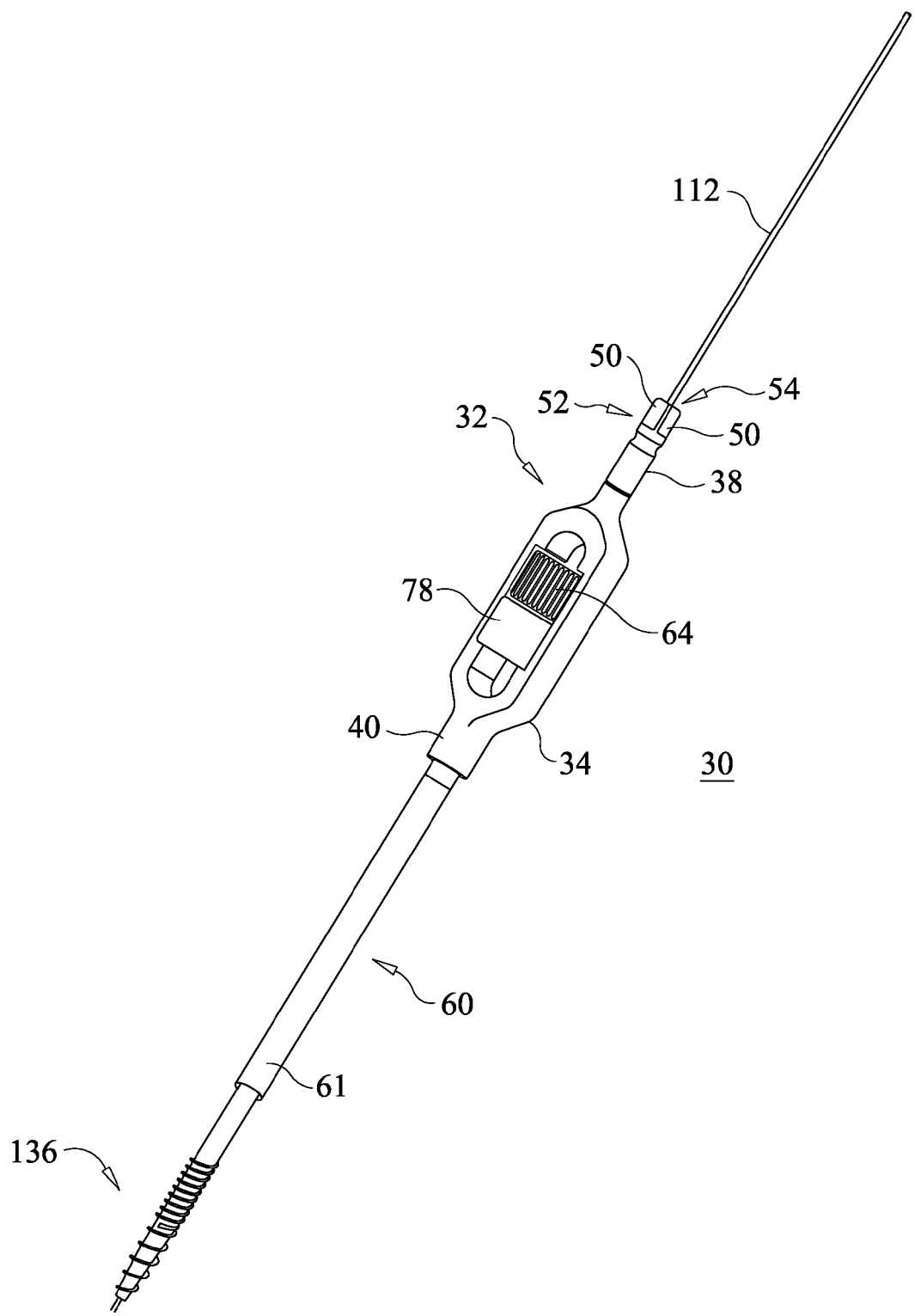
FIG. 1 is a perspective view of components of one embodiment of a surgical implant system in accordance with the principles of the present disclosure.

The exemplary embodiments of a surgical system are discussed in terms of medical devices for the treatment of musculoskeletal disorders and more particularly, in terms of a surgical implant system for delivering and/or fastening implants with a surgical site and a method for treating a spine. In one embodiment, the system includes a surgical instrument including a cannulated driver that is configured to engage a cannulated fastener, such as, for example, a bone screw in a manner such that the cannulae align for disposal of a longitudinal element, such as, for example, a guide wire or a K-wire. In one embodiment, the fastener is a self-tapping cannulated screw. In one embodiment, the driver engages the screw such that the cannula of the driver and the cannula of the screw are coaxial. In some embodiments, the screw has a probe tip, a drill tip, an awl tip, a retractable tip, a cutting flute, a radial cutting flute, a tapered cutting flute and/or a reamer tip.

In one embodiment, the method for treating a spine includes providing a retractable tip instrument for use with a cannulated screw. The cannulated screw has a blunt end opposite a head. A longitudinal element, such as, for example a guide wire or K-wire is positioned through the cannula of the screw such that the guide wire or K-wire extends slightly proud of the blunt end of the screw such that the guide wire or K-wire forms a sharp point tip for the screw. The screw can then be advanced through bone in a single step without first drilling and/or tapping the bone. Once the screw is advanced through the hard cortical bone and is in the vertebral body or cancellous bone of the sacrum, the guide wire or K-wire can be removed so that further advancement through the softer cancellous bone can be achieved without the sharp tip formed by the guide wire or K-wire. This allows a medical practitioner to be more confident that the screw will not drill through the hard cortical bone on the anterior side of the vertebral body or sacrum, because the blunt end of the screw will resist further drilling when the guide wire or K-wire does not extend through the blunt end of the screw.

In one embodiment, the cannulated screw can be implanted into bone by inserting a longitudinal element, such as, for example, a guide wire or K-wire through the cannula of the driver and the cannula of the screw such that the longitudinal element protrudes from a distal end of the cannula. A tip of the longitudinal element is positioned to engage the bone such that the tip creates a pilot hole. The driver engages the screw such that the screw is fixed relative to the driver. In some embodiments, an outer surface of the screw has a hexagonal configuration for engagement with a tool, such as, for example, a driver that may be used to rotate the screw. The screw is rotated relative to the bone such that a portion of the screw rotates within the pilot hole. As the screw rotates within the pilot hole, threads on an outer surface of the screw engage the bone such that the screw penetrates the bone. This allows the screw to be implanted into the bone in a single step.

In one embodiment, the system includes a surgical instrument including a driver and a fastener, such as, for example, a cannulated bone fastener having a threaded outer surface that allows the fastener to penetrate tissue, such as, for example, bone. The cannula of the fastener has a diameter that is greater than an outer surface of the driver such that the driver can be inserted into the cannula of the fastener. When the driver is inserted into the fastener, a distal portion of the driver extends through a distal end of the cannula. A tip of the driver is positioned to engage the bone such that the tip creates a pilot hole. In some embodiments, the tip of the driver includes a sharp point. The fastener is rotated relative to the bone such that a portion of the fastener rotates within the pilot hole. As the fastener rotates within the pilot hole, threads on an outer surface of the fastener engage the bone such that the fastener penetrates the bone. This allows the fastener to be implanted into the bone in a single step.

In one embodiment, the system includes a surgical instrument capable of disassembly to facilitate cleaning of each of the components of the surgical instrument. This configuration provides access to areas of the surgical instrument, including difficult to reach areas and/or inaccessible areas due to a surgical instrument's assembled configuration. In some embodiments, the surgical instrument is capable of disassembly and assembly. In one embodiment, the surgical instrument includes a collet style connection mechanism to facilitate disassembly and assembly. In some embodiments, the surgical instrument may be disassembled and assembled without additional tools or other instruments.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alliteratively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alliterate embodiments are also disclosed. Reference is made in detail to the exemplary embodiments of the present disclosure, which are illustrated in the accompanying figures. Turning to FIGS. 1-26, there are illustrated components of a surgical implant system 30, in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open or mini-open, minimal access and/or minimally invasive including percutaneous surgical technique to deliver and fasten an implant, such as, for example, a bone fastener at a surgical site within a body of a patient, for example, a section of a spine. In one embodiment, the components of system 30 are configured to fix a bone fastener with tissue for a surgical treatment to treat various spine pathologies, such as those described herein.

Figure 2:
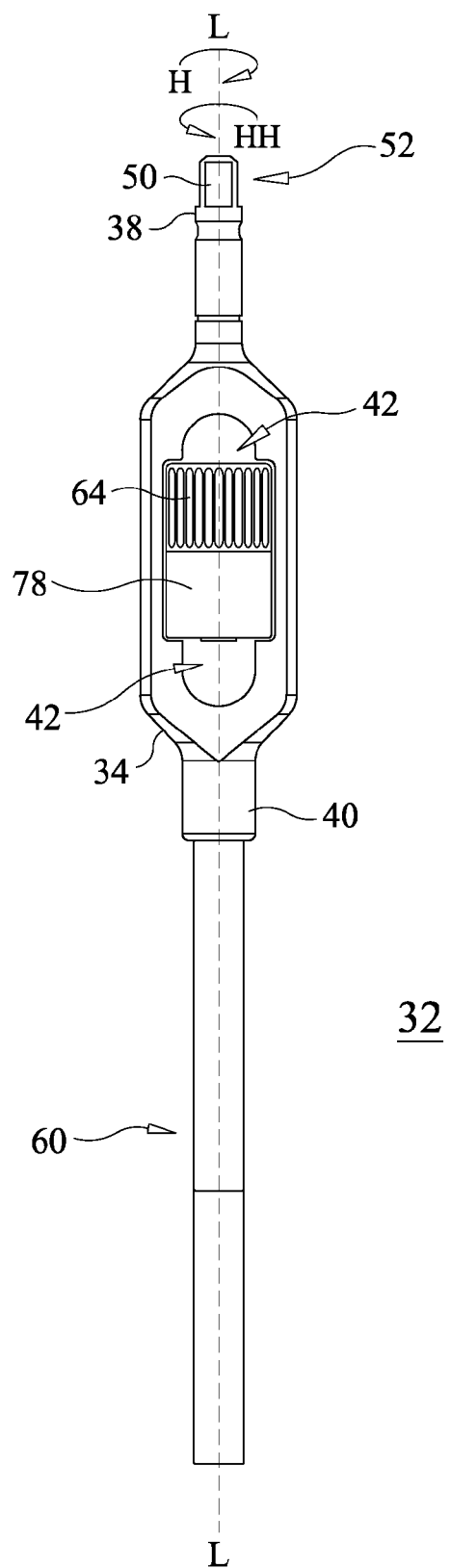
FIG. 2 is a side view of components of the surgical implant system shown in FIG. 1.
Figure 3:
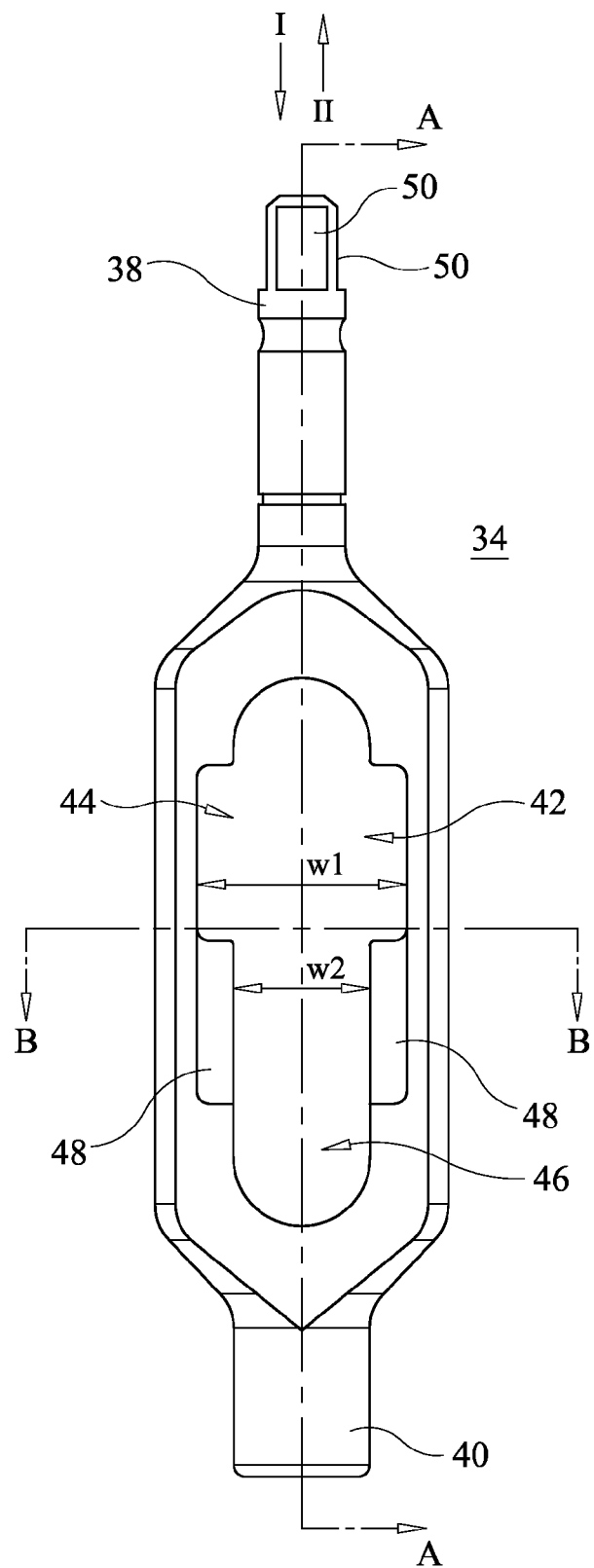
FIG. 3 is a side view of a component of the surgical implant system shown in FIG. 1.
Figure 4:
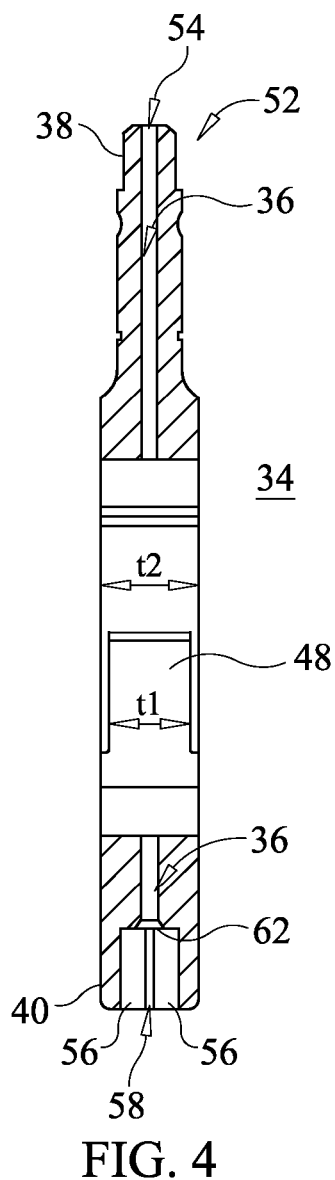
FIG. 4 is a cross section view of a component of the surgical implant system shown in FIG. 3 taken along lines A-A.
Figure 5:
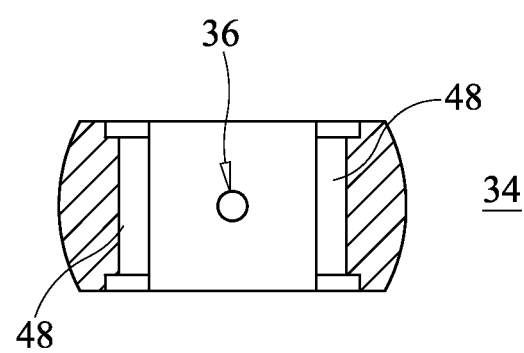
FIG. 5 is a cross section view of a component of the surgical implant system shown in FIG. 3 taken along lines B-B.
Figure 6:
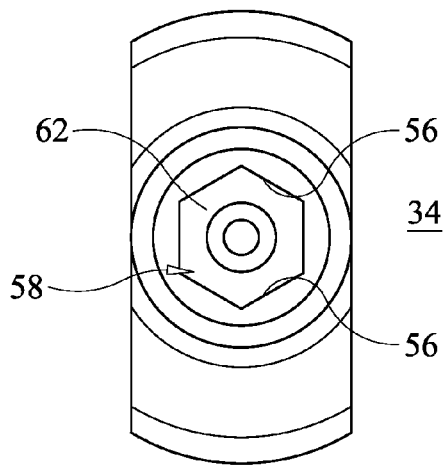
FIG. 6 is an end view of components of the spinal implant system shown in FIG. 1.
Figure 7:
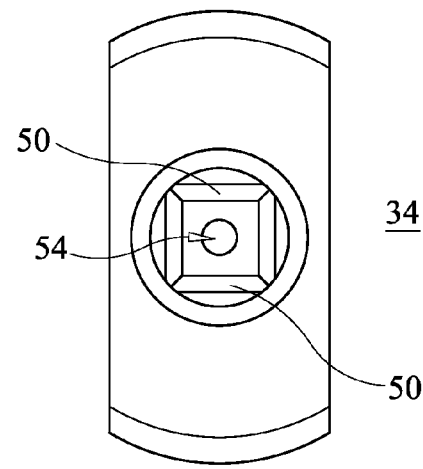
FIG. 7 is an end view of components of the surgical implant system shown in FIG. 1.

System 30 includes a surgical instrument 32 comprising a driver sub-assembly or body 34 including an inner surface defining a passageway 36 extending along a longitudinal axis L through an end 38 of body 34 and an opposite end 40 of body 34, as shown in FIGS. 1 and 2. The inner surface of body 34 defines an opening 42 positioned between ends 38, 40 that is in communication with passageway 36. Opening 42 includes a portion 44 having a width w1 and a portion 46 having a width w2 that is less than width w1, as shown in FIG. 3. Width w2 is defined by the distance between opposite flanges 48. Flanges 48 each have a thickness t1 that is less than a thickness t2 of body 34, as shown in FIG. 4. In some embodiments, passageway 36 has a cylindrical cross section configuration. In some embodiments, passageway 36 has cross section configurations, such as, for example, oval, oblong, triangular, rectangular, square, polygonal, irregular, uniform, non-uniform, variable, tubular and/or tapered.

In some embodiments, end 38 includes a plurality of planar surfaces 50 that define a bit 52 configured for engagement with an instrument, such as, for example a socket tool, a wrench or an actuator configured to rotate instrument 32 about axis L, in the direction shown by arrow H or the direction shown by arrow HH, as shown in FIG. 2. In one embodiment, bit 52 has a square cross section configuration. In some embodiments, bit 52 has square, hexagonal, polygonal, triangular, star or hexalobe cross section configuration. End 38 includes a cavity 54 that extends through bit 52 and is communication with passageway 36. Cavity 54 is centrally positioned with respect to bit 52 such that cavity 54 is equidistant from each of surfaces 50. Cavity 54 is continuous with passageway 36 and has a shape and diameter similar to that of passageway 36.

The inner surface of body 34 includes a plurality of planar surfaces 56 at end 40 that define a socket 58 that is in communication with passageway 36. Socket 58 is configured for disposal of an extension 60 of instrument 32, as described herein, and has a width that is greater than a width of passageway 36 and less than width w2. In one embodiment, socket 58 may have a width that is equal or greater than width w2. In one embodiment, socket 58 has a hexagonal cross section configuration. In some embodiments, socket 58 has square, rectangular, polygonal, triangular, star or hexalobe cross section configuration. End 40 includes a cavity 62 that is communication with socket 58 and passageway 36. Cavity 62 is centrally positioned with respect to socket 58 such that cavity 62 is equidistant from each of surfaces 56. Cavity 62 is continuous with passageway 36 and has a shape and diameter similar to that of passageway 36.

Figure 8:
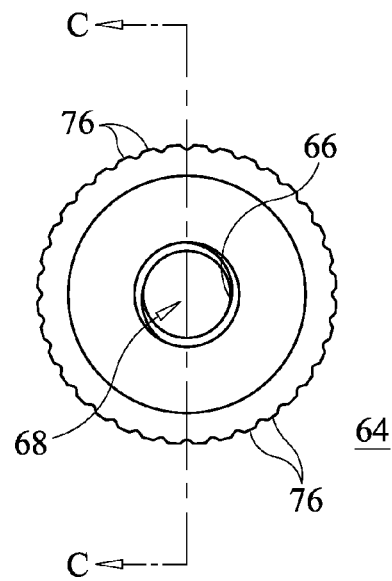
FIG. 8 is an end view of a component of the surgical implant system shown in FIG. 1.
Figure 9:
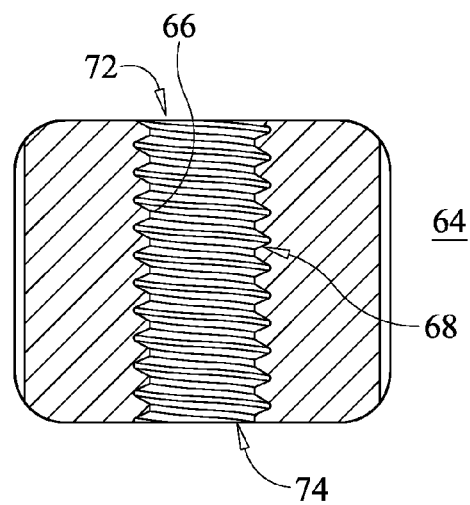
FIG. 9 is a cross section view of a component of the surgical implant system shown in FIG. 8 taken along lines C-C.

A lock, such as, for example, a driver nut or thumbwheel 64 is positioned within portion 44. Thumbwheel 64 includes an inner surface 66 defining a threaded opening or cavity 68, as shown in FIGS. 8 and 9, which is in communication with passageway 36. Cavity 68 is coaxial with passageway 36. Cavity 68 is configured for engagement with a threaded portion of a holding element, such as, for example, a collet 70, as described herein. Cavity 68 has cylindrical cross section and a uniform diameter. Thumbwheel 64 includes opposite openings 72, 74 that are in communication with cavity 68. In some embodiments, cavity 68 is threaded along the entire length of cavity 68. In some embodiments, only a distal portion of cavity 68 is threaded. In some embodiments, cavity 68 may have various cross section configurations, such as, for example, oval, oblong, triangular, rectangular, square, polygonal, irregular, uniform, non-uniform, variable, tubular and/or tapered.

An outer surface of thumbwheel 64 includes a plurality of spaced apart ridges 76 that each extend parallel to axis L. Ridges 76 are configured to facilitate gripping by a medical practitioner. In some embodiments, ridges 76 may be disposed at alternate orientations, relative to axis L, such as, for example, transverse, diamond, perpendicular and/or other angular orientations such as acute or obtuse and/or may be offset or staggered. In some embodiments, the outer surface of thumbwheel 64 may have various surface configurations, such as, for example, smooth and/or surface configurations to enhance gripping by a medical practitioner, such as, for example, rough, arcuate, undulating, porous, semi-porous, dimpled, polished and/or textured.

Figure 10:
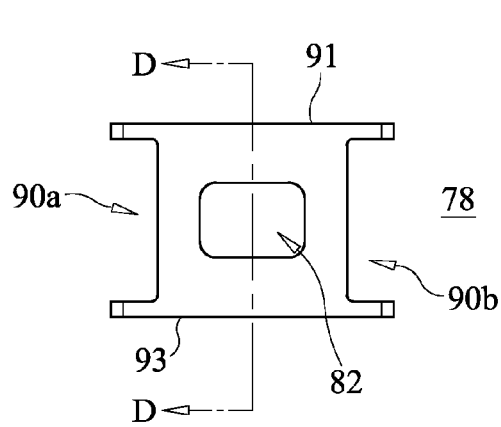
FIG. 10 is an end view of a component of the surgical implant system shown in FIG. 1.
Figure 11:
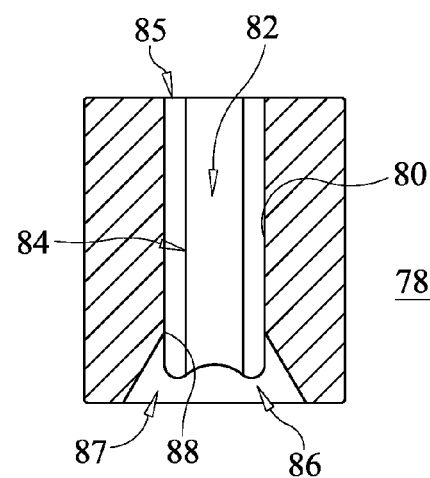
FIG. 11 is a cross section view of a component of the surgical implant system shown in FIG. 10 taken along lines D-D.
Figure 12:
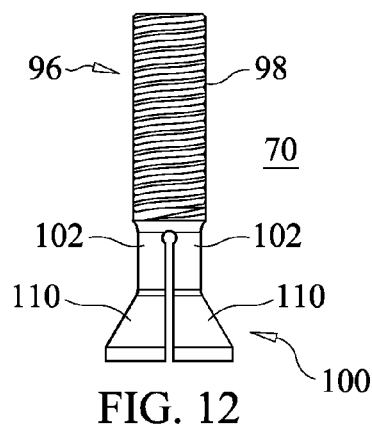
FIG. 12 is a side view of a component of the surgical implant system shown in FIG. 1.

A lock, such as, for example, a driver nut or collar 78 is positioned within portion 46 such that collar 78 is distal to thumbwheel 64. Collar 78 includes an inner surface 80 defining a cavity 82, as shown in FIGS. 10 and 11, which is in communication with cavity 68 and passageway 36. Cavity 82 is coaxial with cavity 68 and passageway 36. Cavity 82 includes a portion 84 and a portion 86. Portion 84 is uniform and has a rectangular cross section with rounded corners. Portion 84 includes an opening 85 that is in communication with cavity 82. Portion 86 includes an opening 87 that is in communication with cavity 82. Portion 86 tapers to an increased diameter in a distal to proximal direction such that portion 86 has a chamfered configuration. Portion 86 has a maximum diameter that is greater than a maximum diameter of portion 84. An interface between portions 84, 86 defines a locking surface 88 configured to engage collet 70, as will be described. In some embodiments, portion 84, portion 86, opening 85 and/or opening 87 may have various cross section configurations, such as, for example, cylindrical, oval, oblong, triangular, rectangular, square, hexagonal, polygonal, irregular, uniform, non-uniform, variable, tubular and/or tapered.

In some embodiments, collar 78 includes a pair of spaced apart grooves 90a, 90b extending between opposite surfaces 91, 93 without extending through surfaces 91, 93. Grooves 90a, 90b extend parallel to one another and are configured to engage flanges 48 to fix collar 78 relative to body 34. To engage flanges 48 with grooves 90a, 90b, collar 78 is positioned in portion 44 such that grooves 90a, 90b are aligned with flanges 48. Collar 78 is translated along axis L, in the direction shown by arrow I in FIG. 3, until collar 78 is positioned in portion 46 and flanges 48 engage grooves 90a, 90b to fix collar 78 with body 34 and resist and/or prevent rotation of collar 78 relative to body 34. Collar 78 may be removed from body 34 by translating collar 78 along axis L, in the direction shown by arrow II in FIG. 3, such that collar 78 moves from portion 46 to portion 44. Collar 78 is removed from body 34 by translating collar 78, in a direction that is transverse to the direction shown by arrows I, II and/or axis L. In some embodiments, collar 78 can be variously connected with body 34, such as, for example, monolithic, integral connection, frictional engagement, threaded engagement, mutual grooves, screws, adhesive, nails, barbs and/or raised element.

Figure 13:
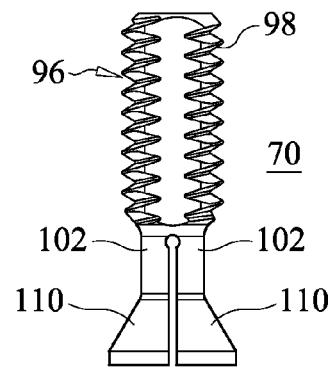
FIG. 13 is a side, cross section view of a component of the surgical implant system shown in FIG. 1.
Figure 14:
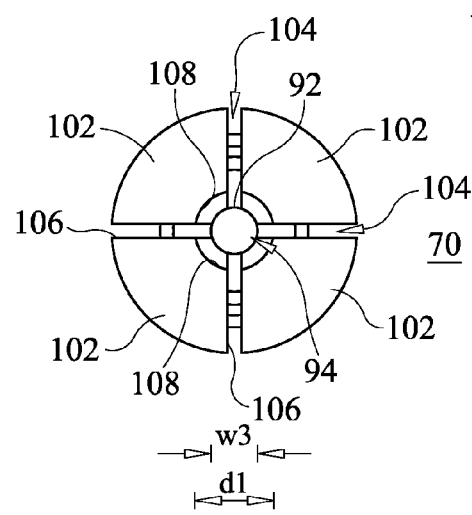
FIG. 14 is an end view of a component of the surgical implant system shown in FIG. 1.

Collet 70 is positioned within passageway 36 and cavities 68, 82. Collet 70 comprises an inner surface 92 defining a passageway 94, as shown in FIGS. 13 and 14, which is in communication with passageway 36 and cavities 68, 82. Passageway 94 is coaxial with passageway 36 and cavities 68, 82. Passageway 94 has a cylindrical cross section configuration and has a uniform diameter along the entire length of passageway 94. Passageway 94 includes openings that are in communication with passageway 36. A section 96 of collet 70 includes a threaded outer surface 98 configured to engage the threads of cavity 68 to fix collet 70 with thumbwheel 64. Section 96 has a cylindrical cross section configuration and has a uniform diameter along the entire length of section 96. In some embodiments, passageway 94 and/or section 96 may have various cross section configurations, such as, for example, oval, oblong, triangular, rectangular, square, polygonal, irregular, uniform, non-uniform, variable, tubular and/or tapered.

A section 100 of collet 70 includes a plurality of cantilevered fingers 102 extending radially outward in a tapered configuration. Fingers 102 taper to an increased diameter in a proximal to distal direction such that section 100 has a substantially conical configuration. Fingers 102 are circumferentially disposed about section 100 and are equidistantly spaced apart. Fingers 102 are spaced apart by a gap 104 defined by opposite planar sidewalls 106. Sidewalls 106 of a respective finger 102 converge at a concave portion 108. Fingers 102 are configured to deflect such that fingers 102 are moveable between a first configuration in which a flared portion 110 of each finger 102 is spaced apart and/or disengaged from surface 88 and a distance d1 between opposite portions 108 is greater than a width w3 of passageway 94 to a second configuration in which portions 110 engage surface 88 for capturing a longitudinal element and a distance between opposite portions 108 is substantially equivalent to width w3.

Figure 16:
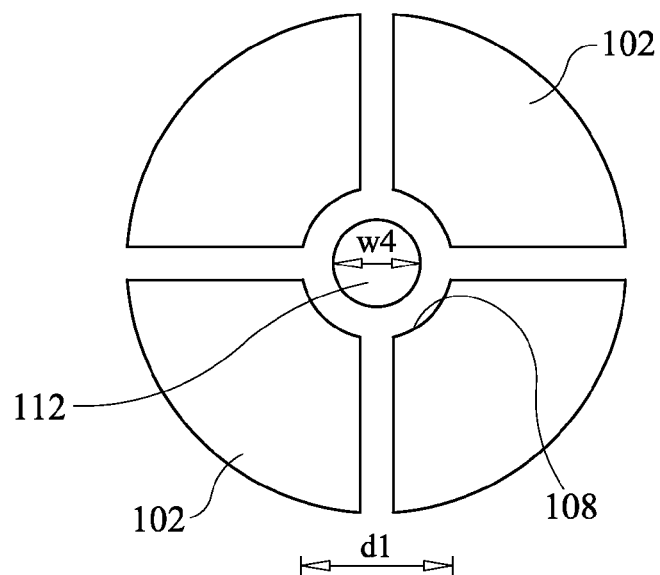
FIG. 16 is a partial cross sectional view of components of the surgical implant system shown in FIG. 15 taken along lines E-E.

A longitudinal element, such as, for example, a K-wire or guide wire 112 is positioned within passageway 36 and cavities 68, 82 and passageway 94 such that at least a tip 114 of guide wire 112 extends through socket 58. Guide wire 112 has a cylindrical cross sectional configuration with a width w4 that is slightly less than width w3 such that guide wire 112 is translatable within passageway 94. Distance d1 is greater than width w4, as shown in FIG. 16. In some embodiments, tip 114 has a sharp point configured to penetrate tissue, such as, for example, cortical or cancellous bone to fix guide wire 112 with the bone and/or create a pilot hole in the bone, as will be described. In some embodiments, tip 114 is beveled. In some embodiments, tip 114 is fluted. In some embodiments, at least a portion of tip 114 is threaded. In some embodiments, at least a portion of tip 114 includes a self-tapping thread. In some embodiments, at least a portion of tip 114 is hollow.

Figure 15:
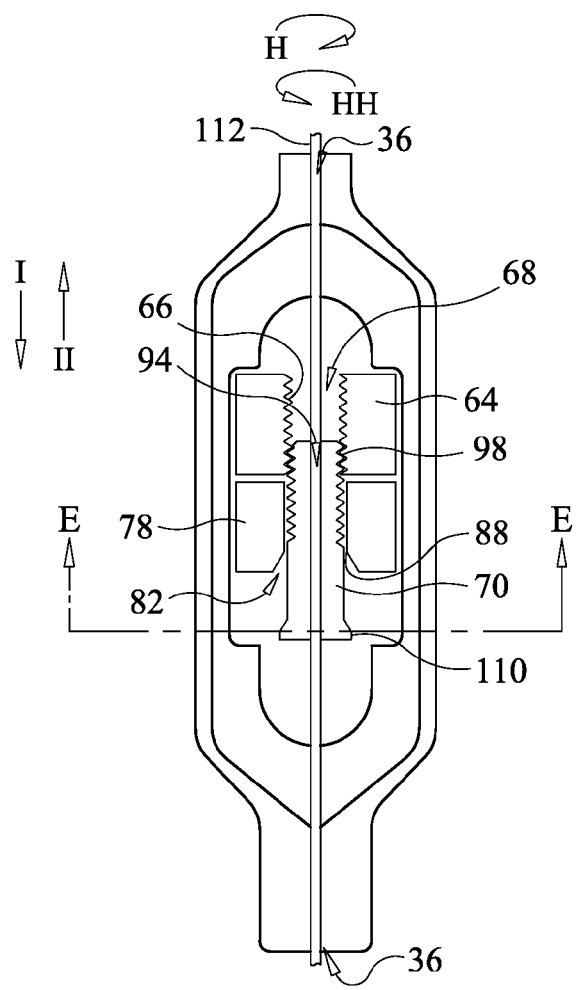
FIG. 15 is a cross section view of components of the surgical implant system shown in FIG. 1.
Figure 17:
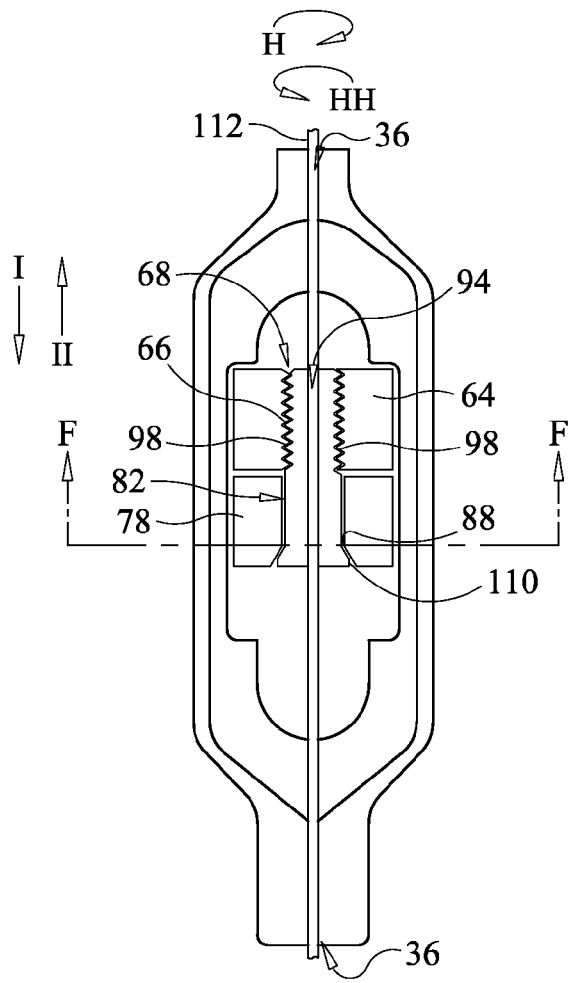
FIG. 17 is a cross section view of components of the surgical implant system shown in FIG. 1.
Figure 18:
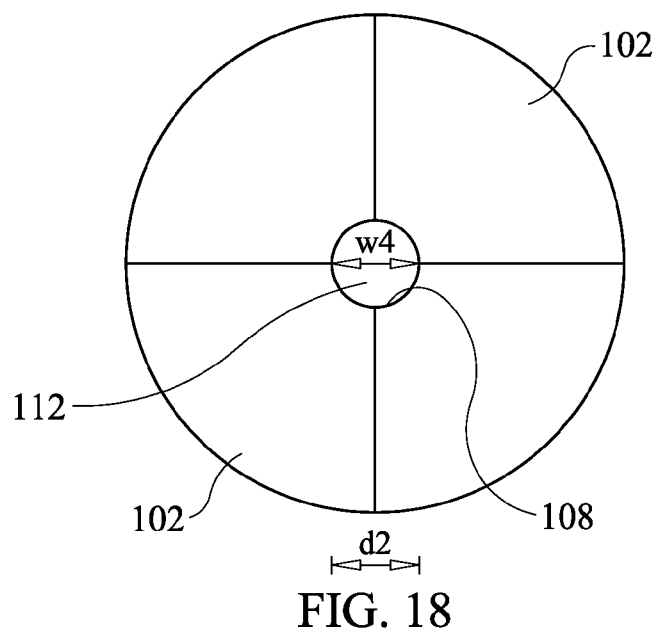
FIG. 18 is a partial cross section view of components of the surgical implant system shown in FIG. 17 taken along lines F-F.

Instrument 32 is movable between a first orientation, as shown in FIGS. 15 and 16, in which portions 110 are spaced apart from surface 88 and guide wire 112 is translatable within passageway 36 and a second orientation, as shown in FIGS. 17 and 18, in which portions 110 engage surface 88 and guide wire 112 is fixed relative to body 34. Instrument 32 moves between the first and second orientations by rotating thumbwheel 64 relative to collar 78, in the direction shown by arrow H or the direction shown by arrow HH. Thumbwheel 64 is rotated relative to collar 78 such that the threads on surface 98 engage the threads on surface 66 such that collet 70 translates along axis L, in the direction shown by arrow I or the direction shown by arrow II.

To move instrument 32 from the first orientation to the second orientation, thumbwheel 64 is rotated, in the direction shown by arrow H or the direction shown by arrow HH, such that collet 70 translates along axis L in the direction shown by arrow II. Collet 70 is translated, in the direction shown by arrow II, until portions 110 engage surface 88, as shown in FIG. 17. As portions 110 engage surface 88, the distance between opposite portions 108 is distance d2, as shown in FIG. 18, which is less than distance d1. Portions 108 engage an outer surface of guide wire 112 when instrument 32 is in the second orientation to fix guide wire 112 relative to collet 70. When instrument 32 is in the second orientation, tip 114 is fixed relative to body 34 such that manipulation of body 34 by, for example, rotating body 34 about axis L causes tip 114 to rotate, in the direction shown by arrow H or the direction shown by arrow HH, such that tip 114 creates a pilot hole in tissue, as described herein.

To move instrument 32 from the second orientation to the first orientation, thumbwheel 64 is rotated, in the direction shown by arrow H or the direction shown by arrow HH, such that collet 70 translates along axis L, in the direction shown by arrow I. Collet 70 is translated in the direction shown by arrow I until portions 110 are spaced apart from surface 88, as shown in FIG. 15. As portions 110 disengage surface 88, the distance between opposite portions 108 increases from distance d2 to distance d1, as shown in FIG. 16. When instrument 32 is in the first orientation, guide wire 112 is translatable along axis L within passageway 36 and passageway 94 such that the length of guide wire 112 that extends distally beyond socket 58 can be selectively adjusted. Once the selected length of guide wire 112 extends through socket 58, instrument 32 is moved from the first orientation to the second orientation to fix guide wire 112 relative to body 34.

Extension 60 is positioned in socket 58. Extension 60 comprises an inner surface defining a channel 118 that is in communication with passageway 36. Channel 118 has cylindrical cross section and a uniform diameter. Extension 60 includes opposite openings 120, 122 that are in communication with channel 118. In some embodiments, channel 118 may have various cross section configurations, such as, for example, oval, oblong, triangular, rectangular, square, polygonal, irregular, uniform, non-uniform, variable, tubular and/or tapered.

An end 124 of extension 60 includes a plurality of planar surfaces 126 that define a bit 128 configured for disposal in socket 58 in a manner that prevents extension 60 from rotating relative to body 34. In one embodiment, bit 128 has a hexagonal cross section configuration. In some embodiments, bit 128 has square, rectangular, polygonal, star or hexalobe cross section configuration, depending upon the configuration of socket 58. Opening 120 extends through bit 128 and is centrally positioned with respect to bit 128 such that opening 120 is equidistant from each of surfaces 126. In some embodiments, extension 60 can be variously connected with body 34, such as, for example, monolithic, integral connection, frictional engagement, threaded engagement, mutual grooves, screws, adhesive, nails, barbs and/or raised element. In some embodiments, extension 60 is welded to body 34. In one embodiment, the weld between extension 60 and body 34 is configured to withstand axial loading and torque.

A second end 130 of extension 60 includes a plurality of planar surfaces 132 that define a bit 134 configured to engage a fastener, such as, for example, a bone screw 136. In one embodiment, bit 134 has a hexagonal cross section configuration. In some embodiments, bit 134 has square, rectangular, polygonal, star or hexalobe cross section configuration. Opening 122 extends through bit 134 and is centrally positioned with respect to bit 134 such that opening 122 is equidistant from each of surfaces 132.

Figure 19:
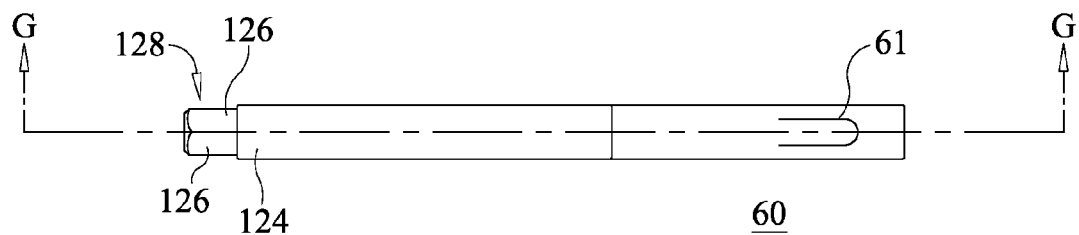
FIG. 19 is a side view of a component of the surgical implant system shown in FIG. 1.
Figure 20:
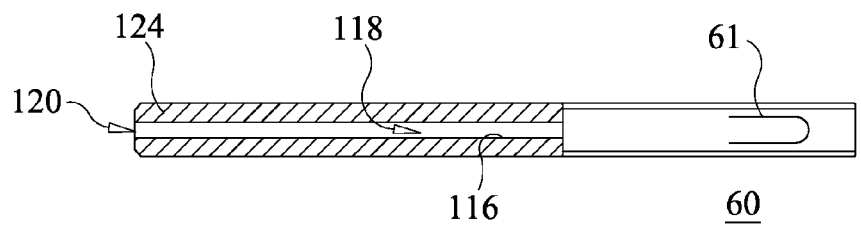
FIG. 20 is a cross section view of a component of the surgical implant system shown in FIG. 19 taken along lines G-G.
Figure 21:
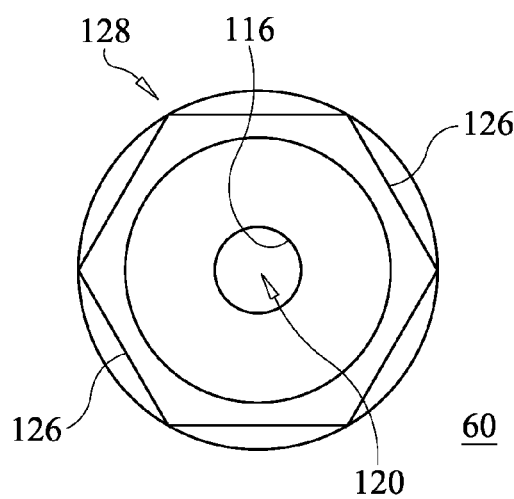
FIG. 21 is an end view of a component of the surgical implant system shown in FIG. 1.
Figure 22:
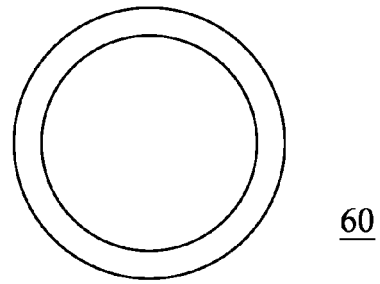
FIG. 22 is an end view of a component of the surgical implant system shown in FIG. 1.
Figure 23:
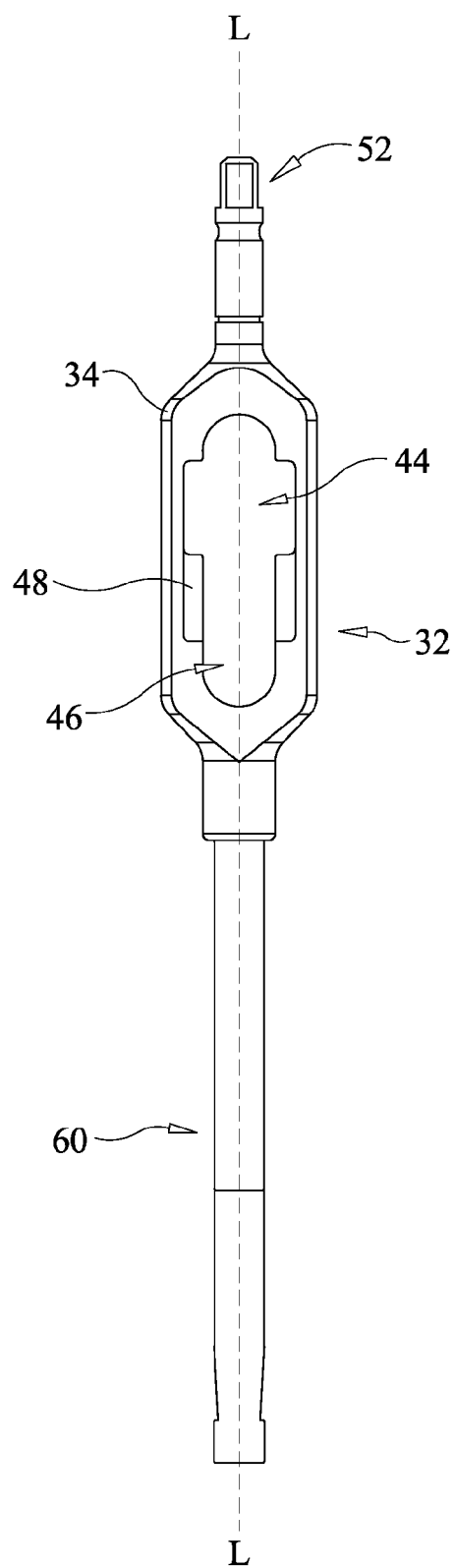
FIG. 23 is a side view of components of the surgical implant system shown in FIG. 1.
Figure 24:
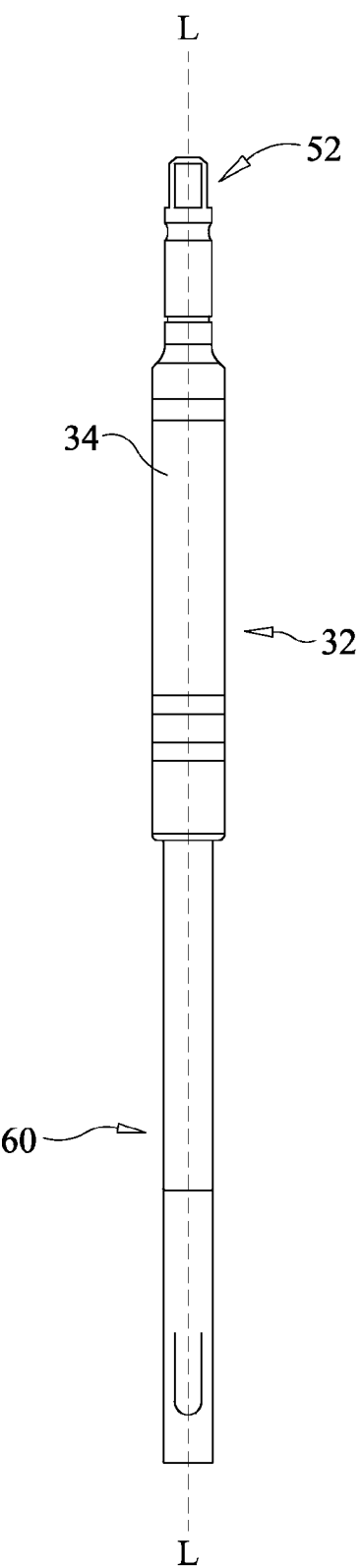
FIG. 24 is a side view of components of the surgical implant system shown in FIG. 1.

In some embodiments, extension 60 includes a cut out portion defining a spring 61 configured to provide friction to post 172 of a screw 136 to fix screw 136 with extension 60. In some embodiments, spring 61 is resiliently biased inwardly, as shown in FIG. 19. In some embodiments, extension 60 includes a pair of springs 61 positioned on opposite sides of extension 60. In some embodiments, extension 60 includes one or a plurality of springs 61. In some embodiments, springs 61 are evenly spaced apart and are disposed radially about extension 60. In some embodiments, extension 60 can be variously connected with screw 136, such as, for example, frictional engagement, threaded engagement, mutual grooves, screws, adhesive, nails, barbs and/or raised element.

Figure 25:
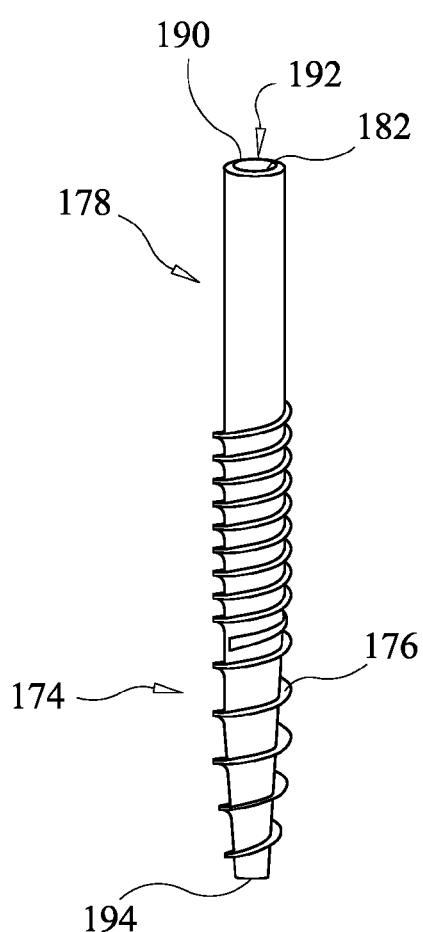
FIG. 25 is a perspective view of a component of the surgical implant system shown in FIG. 1.
Figure 26:
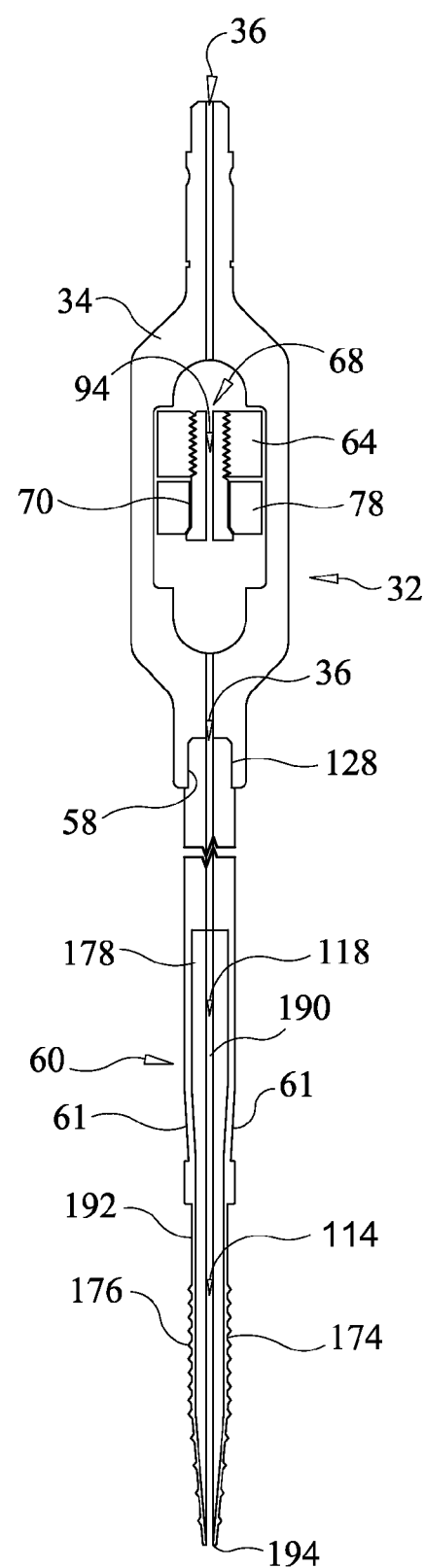
FIG. 26 is a side, cross sectional view of components of the surgical implant system shown in FIG. 1.

In some embodiments, as shown in FIGS. 1, 25 and 26, screw 136 is a posted TSRH screw comprising a bone engaging portion 174 having a threaded outer surface 176 configured to penetrate tissue, such as, for example, bone. Screw 136 comprises an unthreaded post 178 proximal of portion 174. Post 178 is fixed relative to portion 174. Screw 136 includes an inner surface 190 defining a cylindrical channel 192 extending through and between post 178 and a tip 194 of screw 136 along axis L. In some embodiments, post 178 includes a hexagonal tool socket 182 configured for disposal of a tool, such as, for example, a hexagonal driver, configured to rotate screw 136 about axis L. In some embodiments, channel 192 and/or socket 182 may have various cross section configurations, such as, for example, circular, oval, oblong, triangular, rectangular, square, polygonal, irregular, uniform, non-uniform, variable, tubular and/or tapered.

In assembly, operation and use, a surgical implant system, similar to system 30 described herein, is employed with a surgical procedure for treatment of a spinal disorder affecting a section of a spine of a patient, as discussed herein. For example, system 30 can be used with a surgical procedure for treatment of a condition or injury of an affected section of the spine including vertebrae. In some embodiments, one or all of the components of system 30 can be delivered as a pre-assembled device or can be assembled in the OR. System 30 may be completely or partially revised, removed or replaced.

For example, system 30 can be employed with a surgical treatment of an applicable condition or injury of an affected section of a spinal column and adjacent areas within a body, such as, for example, vertebrae. In some embodiments, system 30 may be employed with one or a plurality of vertebra. To treat a selected section of the vertebrae, a medical practitioner obtains access to a surgical site including the vertebrae in any appropriate manner, such as through incision and retraction of tissues. In some embodiments, system 30 can be used in any existing surgical method or technique including open surgery, mini-open surgery, minimally invasive surgery including percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of implantable components of system 30 such as, for example, screw 136. A preparation instrument (not shown) can be employed to prepare tissue surfaces of vertebrae, as well as for aspiration and irrigation of a surgical region.

Collar 78 is positioned in portion 44 such that grooves 90a, 90b are aligned with flanges 48 and cavity 82 is coaxial with passageway 36. Collar 78 is translated along axis L, in the direction shown by arrow I in FIG. 3, such that collar 78 is positioned in portion 46 and flanges 48, 48 engage grooves 90a, 90b to fix collar 78 with body 34 and prevent rotation of collar 78 relative to body 34. Thumbwheel 64 is positioned to engage collar 78 such that a distal surface of thumbwheel 64 engages a proximal surface of collar 78 and cavities 68, 82 are coaxial. In some embodiments, thumbwheel 64 may engage collar 78 either before or after flanges 48 are disposed in grooves 90a, 90b.

Collet 70 is positioned within cavities 68, 82 by inserting a proximal end of collet 70 through opening 87 and translating collet 70 along axis L, in the direction shown by arrow II in FIG. 3, such that the proximal end of collet 70 is positioned within cavity 68 and threads on surface 98 engage threads on surface 66. Thumbwheel 64 is rotated, in the direction shown by arrow H or the direction shown by arrow HH, such that collet 70 translates within cavities 68, 82, in the direction shown by arrow II, and instrument 32 is disposed in the first orientation, as shown in FIG. 15.

Extension 60 is positioned relative to body 34 such that bit 134 is aligned or coaxial with socket 58. Extension 60 is translated along axis L relative to body 34, in the direction shown by arrow II, such that bit 134 is disposed in socket 58 to prevent rotation of extension 60 relative to body 34 and passageway 36 is aligned or coaxial with channel 118. In some embodiments, an interface between extension 60 and body 34 is welded to fix extension relative to body 34.

Screw 136 is positioned relative to extension 60 such that post 178 is positioned within channel 118. Post 178 is translated within channel 118, in the direction shown by arrow II, such that springs 61 are biased to fix post 178 relative to extension 60.

When post 178 is disposed in extension 60, channels 118, 188 are aligned or coaxial. Tip 114 is inserted through cavity 54 and translated relative to body 34, in the direction shown by arrow I, such that guide wire 112 extends through passageways 36, 94 and channels 118, 192 and at least a portion of tip 114 extends distal to tip 194.

To fix the position of guide wire 112 relative to instrument 32 and/or screw 136, instrument 32 is moved from the first orientation, as shown in FIG. 15, to the second orientation, as shown in FIG. 17, by rotating thumbwheel 64, in the direction shown by arrow H or the direction shown by arrow HH, such that collet 70 translates along axis L, in the direction shown by arrow II. Collet 70 is translated, in the direction shown by arrow II such that portions 110 engage surface 88, as shown in FIG. 17. As portions 110 engage surface 88, portions 108 engage an outer surface of guide wire 112 to fix guide wire 112 relative to collet 70.

System 30 is delivered through the surgical pathway to a location adjacent the vertebrae at a surgical site such that tip 114 penetrates an outer layer of cortical bone of vertebrae, for example, a posterior side of the vertebrae to create a pilot hole. In one embodiment, tip 114 penetrates cortical bone adjacent a posterior side of a sacrum. The depth of the pilot hole may be increased by driving body 34, in the direction shown by arrow I in FIG. 3 by, for example, impacting bit 52 with a blunt instrument, such as, for example, a mallet or hammer. The depth of the pilot hole may also be increased by rotating screw 136 about axis L, in the direction shown by arrow H or the direction shown by arrow HH, by rotating nut 196 and/or a hexagonal portion 175 of collar 174 with a tool, such as, for example, a driver.

As the depth of the pilot hole increases, thread form 184 engages the outer layer of cortical bone such that further rotation of screw 136 about axis L causes tip 194 to move through the pilot hole and the outer layer of cortical bone and into a layer of cancellous bone. Screw 136 is rotated until the shaft of screw 136 penetrates the vertebra to fix screw 136 with the tissue. This configuration implants and fixes screw 136 with the tissue including bone in a single step.

In some embodiments, instrument 32 is moved from the second orientation to the first orientation after tip 114 penetrates the outer layer of cortical bone. Tip 114 is retracted into channel 192, for example, such that tip 114 no longer extends distal to tip 194. After tip 114 is retracted, instrument 32 is moved from the first orientation to the second orientation to maintain tip 114 within channel 192. Screw 136 is rotated to allow further insertion of screw 136 into the vertebra. This configuration allows screw 136 to penetrate cancellous bone, while preventing screw 136 from penetrating an inner layer of cortical bone positioned distal to the layer of cancellous bone in the event screw 136 engages the inner layer of cortical bone during insertion of screw 136 into the vertebra.

In some embodiments, after screw 136 is advanced through a first layer, such as, for example, cortical bone of a posterior side of vertebrae, such as, for example, a sacrum, and is disposed in a second layer of a vertebral body, such as, for example, cancellous bone of the sacrum. This configuration facilitates removal of tip 114 from the tissue such that screw 136 can be advanced through the softer cancellous tissue without tip 114. This configuration resists and/or prevents penetration and/or pass through of tip 114 and/or screw 136 through a third layer, such as, for example, cortical bone of an anterior side of vertebrae, for example, the sacrum. In one embodiment, a blunt end of screw 136 resists and/or prevents further penetration of cortical bone.

The components of system 30, including instrument 32 and screw 136 are employed to augment one or more surgical treatments. Instrument 32, including extension 60, may be disengaged from screw 136 and removed from the surgical site. To disengage screw 136 from extension 60, post 178 is translated, in the direction shown by arrow I, relative to extension 60 such that springs 61 disengage recesses 178. Extension 60 is translated along axis L, in the direction shown by arrow II, such that extension 60 is spaced apart from post 178.

Figure 27:
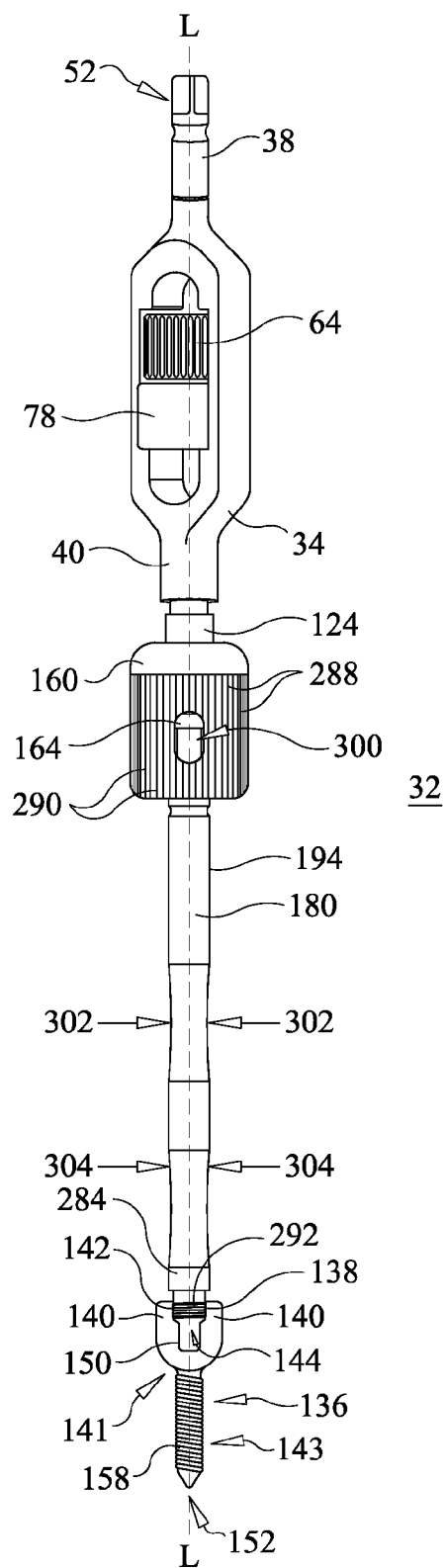
FIG. 27 is a side view of components of one embodiment of a surgical implant system in accordance with the principles of the present disclosure.

In one embodiment, as shown in FIG. 27, screw 136 includes a pair of spaced apart arms 140. An inner surface of each of arms 140 includes a thread form 142 configured to engage thread form 138 to fix extension 60 with screw 136. Arms 140 define a U-shaped cavity 144. Cavity 144 is configured for disposal of a spinal construct, such as, for example, a vertebral rod that connects one or more bone fasteners, such as, for example, screws 136. Screw 136 includes an opening 141 that is coaxial with axis L.

Screw 136 includes a bone penetrating portion 143 disposed in opening 141 such that cavity 144 is rotatable relative to portion 143. In some embodiments, screw 136 may include a mono-axial screw or multi-axial screw. An inner surface of portion 143 defines a channel that is in communication with channel 118 and passageways 36, 94. The channel in portion 143 is coaxial with channel 118 and passageways 36, 94. The channel in portion 143 is configured for moveable disposal of guide wire 112. The channel in portion 143 has cylindrical cross section and a uniform diameter. Portion 143 includes opposite openings 150, 152 that are in communication with the channel in portion 143. In some embodiments, the channel in portion 143 may have various cross section configurations, such as, for example, oval, oblong, triangular, rectangular, square, polygonal, irregular, uniform, non-uniform, variable, tubular and/or tapered.

An outer surface of screw 136 includes a thread form 158 configured to penetrate tissue, such as, for example, bone. In one embodiment, socket 156 has a hexagonal cross section configuration. In some embodiments, thread form 158 is a self-tapping thread.

In one embodiment, the intermediate portion of extension 60 positioned between ends 124, 130 is free of threads and end 124 includes a hub 160. End 124 further includes a flange 164 having an increased width. In some embodiments, hub 160 includes an inner surface defining a passageway configured for disposal of end 124 such that hub 160 is translatable relative to end 124, in the direction shown by arrow I and/or the direction shown by arrow II, and is rotatable relative to axis L in the direction shown by H and/or the direction shown by arrow HH. The passageway in hub 160 has a maximum width that is less than flange 164 such that hub 160 is prevented from translating, in the direction shown by arrow I, relative to flange 164. In some embodiments, the inner surface of hub 160 and an outer surface of end 124 each include threads configured to mate with one another to fix hub 160 relative to end 124. In some embodiments, hub 160 can be variously connected with end 124, such as, for example, monolithic, integral connection, frictional engagement, threaded engagement, mutual grooves, screws, adhesive, nails, barbs and/or raised element.

Instrument 32 includes a sleeve 180 extending between an end 282 and an opposite end 284. Sleeve 180 includes an inner surface defining a passageway configured for disposal of extension 60. End 282 includes an enlarged gripping portion 288 having a plurality of spaced apart ridges 290 that each extend parallel to axis L. Ridges 290 are configured to facilitate gripping by a medical practitioner. In some embodiments, ridges 290 may be disposed at alternate orientations, relative to axis L, such as, for example, transverse, diamond, perpendicular and/or other angular orientations such as acute or obtuse and/or may be offset or staggered. An inner surface of gripping portion 288 has a thread form configured to engage the threads on hub 160 to fix sleeve 180 relative to hub 160. In some embodiments, hub 160 can be variously connected with sleeve 180, such as, for example, monolithic, integral connection, frictional engagement, threaded engagement, mutual grooves, screws, adhesive, nails, barbs and/or raised element.

End 284 includes a thread form 292 configured to engage thread form 142 to engage sleeve 180 with screw 136. In some embodiments, sleeve 180 can be variously connected with screw 136, such as, for example, frictional engagement, threaded engagement, mutual grooves, screws, adhesive, nails, barbs and/or raised element.

In some embodiments, gripping portion 188 includes at least one oblong opening 300 extending through inner and outer surfaces of gripping portion 288 configured to provide visualization of end 124. Gripping portion 288 may include one or a plurality of openings 300. In some embodiments, openings 300 are circumferentially disposed about gripping portion 288. In some embodiments, openings 300 are variously shaped, such as, for example, circular, oval, triangular, square, polygonal, irregular, uniform, non-uniform, offset, staggered, undulating, arcuate, variable and/or tapered.

In some embodiments, a shaft 194 of sleeve 180 includes at least one oblong opening 302 extending through inner and outer surfaces of shaft 194 configured to provide visualization of the intermediate portion of extension 60. In some embodiments, shaft 194 includes at least one oblong opening 304 extending through inner and outer surfaces of shaft 194 configured to provide visualization of end 130. Shaft 194 may include one or a plurality of openings 302 and/or openings 304. In some embodiments, openings 302 and/or openings 304 are circumferentially disposed about shaft 194. In some embodiments, openings 302, 304 are aligned axially. In some embodiments, openings 300, 302, 304 are aligned axially. In some embodiments, openings 302 and/or openings 304 are variously shaped, such as, for example, circular, oval, triangular, square, polygonal, irregular, uniform, non-uniform, offset, staggered, undulating, arcuate, variable and/or tapered.

An incision is made in the body of a patient and a cutting instrument (not shown) creates a surgical pathway for delivery of implantable components of system 30 such as, for example, screw 136, as shown in FIG. 27. A preparation instrument (not shown) can be employed to prepare tissue surfaces of vertebrae, as well as for aspiration and irrigation of a surgical region. Collar 78 and thumbwheel 64 engage body 34 as described above; collet 70 is positioned within channels 68, 82 as described above; and extension 60 engages body 34 as described above. Screw 136 is positioned relative to extension 60 such that thread form 292 is aligned with thread form 142. Body 34 is rotated relative to channel 144, in the direction shown by arrow H or the direction shown by arrow HH, to engage sleeve 180 with screw 136 such that passageways 36, 94, channel 118 and the passageway in portion 143 are aligned. Tip 114 is inserted through cavity 54 and translated relative to body 34, in the direction shown by arrow I, such that guide wire 112 extends through passageways 36, 94, channel 118 and the passageway of portion 143 and at least a portion of tip 114 extends distal to opening 152.

To fix the position of guide wire 112 relative to instrument 32 and/or screw 136, instrument 32 is moved from the first orientation, as shown in FIG. 15, to the second orientation, as shown in FIG. 17, by rotating thumbwheel 64, in the direction shown by arrow H or the direction shown by arrow HH, such that collet 70 translates along axis L, in the direction shown by arrow II. Collet 70 is translated, in the direction shown by arrow II, such that portions 110 engage surface 88, as shown in FIG. 17. As portions 110 engage surface 88, portions 108 engage an outer surface of guide wire 112 to fix guide wire 112 relative to collet 70.

System 30 is delivered through the surgical pathway to a location adjacent the vertebrae at a surgical site such that tip 114 penetrates an outer layer of cortical bone of vertebrae to create a pilot hole. The depth of the pilot hole may be increased by driving body 34, in the direction shown by arrow I in FIG. 3, by, for example, impacting bit 52 with a blunt instrument. The depth of the pilot hole may also be increased by rotating portion 143 about axis L, in the direction shown by arrow H or the direction shown by arrow HH.

As the depth of the pilot hole increases, thread form 158 engages the outer layer of cortical bone such that further rotation of screw 136 about axis L causes a tip of portion 143 to move through the pilot hole and the outer layer of cortical bone and into a layer of cancellous bone. Screw 136 is rotated until portion 143 penetrates the vertebrae to fix screw 136 with the tissue. This configuration implants and fixes screw 136 with the tissue including bone in a single step.

In one embodiment, instrument 32 is disassembled to facilitate cleaning of one or all of the components of instrument 32. The configuration of the collet connection of instrument 32 provides access to areas of instrument 32, including difficult to reach areas and/or inaccessible areas due to its assembled configuration. Instrument 32 may be re-assembled for use in a surgical procedure. In some embodiments, system 30 may comprise various instruments including the locks and collet configuration of the present disclosure, with, for example, inserters, extenders, reducers, spreaders, distractors, blades, retractors, clamps, forceps, elevators and drills, which may be alternately sized and dimensioned, and arranged as a kit.

Upon completion of a procedure, the surgical instruments, assemblies and non-implanted components of system 30 are removed and the incision(s) are closed. One or more of the components of system 30 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 30. In some embodiments, system 30 may include one or a plurality of plates, connectors and/or bone fasteners for use with a single vertebral level or a plurality of vertebral levels.

In one embodiment, system 30 includes an agent, which may be disposed, packed, coated or layered within, on or about the components and/or surfaces of system 30. In some embodiments, the agent may include bone growth promoting material, such as, for example, bone graft to enhance fixation of the components and/or surfaces of system 30 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a lock including an inner surface defining a cavity and a locking surface;
   a holding element positioned within the cavity and comprising a distal end including a plurality of fingers, the holding element including an inner surface defining a passageway; and
   a longitudinal element positioned within the passageway and the cavity,
   wherein the surgical instrument includes a first orientation in which the fingers are spaced apart from the locking surface and the longitudinal element and the longitudinal element is translatable relative to the holding element and a second orientation in which the fingers engage the locking surface to engage the fingers with the longitudinal element to fix the longitudinal element relative to the holding element.

2. A surgical instrument as recited in claim 1, wherein the lock comprises a first lock and a second lock such that the locks relatively rotate between the orientations.

3. A surgical instrument as recited in claim 2, further comprising a body that supports the locks and comprises a pair of flanges and the lock comprises a pair of grooves configured for slidable engagement with the flanges.

4. A surgical instrument as recited in claim 3, wherein a proximal end of the body comprises a bit configuration.

5. A surgical instrument as recited in claim 3, wherein a distal end of the body comprises an aperture; and further comprising an extension positioned in the aperture, the extension comprising an inner surface defining a channel.

6. A surgical instrument as recited in claim 5, wherein an outer surface of the extension includes a thread form configured to engage a thread form of a fastener to fix the fastener with the extension.

7. A surgical instrument as recited in claim 2, wherein an inner surface of the second lock comprises a first thread form and a proximal end of the holding element comprises a second thread form configured to engage the first thread form between the first and second orientations.

8. A surgical instrument as recited in claim 1, wherein the fingers extend radially outward in a tapered configuration.

9. A surgical instrument as recited in claim 8, wherein the fingers are circumferentially disposed about the distal end of the holding element.

10. A surgical instrument as recited in claim 8, wherein the fingers extend from the distal end of the holding element in a cantilevered configuration.

11. A surgical instrument as recited in claim 8, wherein the fingers taper to an increased diameter of the holding element in a proximal to distal direction.

12. A surgical instrument as recited in claim 8, wherein the fingers are spaced apart from one another when the surgical instrument is in the first orientation and the fingers each engage adjacent ones of the fingers when the surgical instrument is in the second orientation.

13. A surgical instrument as recited in claim 1, wherein the inner surface of the lock includes a distal portion having a chamfered configuration.

14. A method for treating a spine, the method comprising the steps of:
   providing a surgical instrument comprising a lock including an inner surface defining a cavity and a locking surface, and a holding element positioned within the cavity and comprising an inner surface defining a passageway;
   providing a fastener including an inner surface defining an axial passageway;
   connecting the fastener with the surgical instrument;
   disposing a longitudinal element within the cavity and the passageways such that a tip of the longitudinal element extends from the fastener;
   engaging the tip with tissue that includes a first layer, a second layer and a third layer such that the tip penetrates the first layer and/or the second layer;
   moving the holding element to engage the locking surface to fix the longitudinal element with the holding element;
   engaging the surgical instrument with the fastener such that the fastener moves relative to the longitudinal element and penetrates the first and second layers; and
   removing the longitudinal element from the passageway of the fastener.

15. A method as recited in claim 14, wherein the step of engaging the tip with tissue includes resisting penetration of the tip with the third layer.

16. A method as recited in claim 14, wherein the step of engaging the surgical instrument with the fastener includes preventing penetration of the fastener with the third layer.

17. A method as recited in claim 14, wherein the first layer includes cortical bone, the second layer includes cancellous bone and the third layer includes cortical bone.

18. A surgical system comprising:
   a surgical instrument comprising:
      a body comprising an inner surface defining a first passageway, an opening and an aperture, the opening and the aperture being in communication with the first passageway,
      a lock positioned within the opening and including an inner surface defining a cavity that is in communication with the first passageway, the lock including a locking surface,
      a holding element positioned within the cavity comprising a distal end including a plurality of fingers, the holding element including an inner surface defining a second passageway that is in communication with the first passageway, and
      an extension positioned in the aperture, the extension comprising an inner surface defining a first channel that is in communication with the first passageway;
   a fastener engaging the extension, the fastener comprising an inner surface defining a second channel; and
   a longitudinal element positioned within the passageways, the cavity and the channels such that at least a tip of the longitudinal element extends through a distal end of the second channel,
   wherein the surgical instrument includes a first orientation in which the fingers are each spaced apart from the locking surface and the longitudinal element and the longitudinal element is translatable relative to the body and a second orientation in which the fingers each engage the locking surface such that the fingers engage the longitudinal element to fix the longitudinal element relative to the body.

19. A surgical system as recited in claim 18, wherein a proximal portion of the fastener is configured for disposal within the first channel.

20. A surgical system as recited in claim 18, wherein a distal end of the extension has a bit configuration that is disposed in a recess defined by the inner surface of the fastener to prevent rotation of the fastener relative to the extension.

* * * * *